United States Patent
Gardon-Mollard et al.

(10) Patent No.: US 6,430,970 B1
(45) Date of Patent: Aug. 13, 2002

(54) COMPRESSIVE ORTHOSIS SUCH AS RETENTION STOCKING OR TIGHTS

(75) Inventors: Christian Gardon-Mollard, Chamalieres (FR); Francois Guyot, Saint Blaise (CH)

(73) Assignee: Innothera Topic International, Arcueil (FR)

( * ) Notice: Subject to any disclaimer, the term of this patent is extended or adjusted under 35 U.S.C. 154(b) by 0 days.

(21) Appl. No.: 09/720,813

(22) PCT Filed: Jul. 1, 1999

(86) PCT No.: PCT/FR99/01585

§ 371 (c)(1),
(2), (4) Date: Jul. 16, 2001

(87) PCT Pub. No.: WO00/01332

PCT Pub. Date: Jan. 13, 2000

(30) Foreign Application Priority Data

Jul. 6, 1998 (FR) .............................................. 98 08638

(51) Int. Cl.[7] .............................................. A41B 11/00
(52) U.S. Cl. ..................................... 66/178 A; 66/178 R
(58) Field of Search ............................... 66/178 A, 183, 66/172 E, 178 R; 602/63, 62; 2/239, 61, 22, 240, 241, 242

(56) References Cited

U.S. PATENT DOCUMENTS

| | | | |
|---|---|---|---|
| 3,889,494 A | | 6/1975 | Patience et al. |
| 4,027,667 A | * | 6/1977 | Swallow et al. .............. 66/178 |
| 4,048,818 A | * | 9/1977 | Cueman ...................... 66/178 |
| 4,172,456 A | * | 10/1979 | Zens ........................... 66/178 |
| 4,502,301 A | * | 3/1985 | Swallow et al. .............. 66/178 |
| 4,745,917 A | | 5/1988 | Hasty et al. |
| 5,412,957 A | * | 5/1995 | Bradberry et al. ............ 66/178 |
| 6,012,177 A | * | 1/2000 | Cortinovis ................... 66/178 |

FOREIGN PATENT DOCUMENTS

| | | |
|---|---|---|
| FR | 2 654 925 A1 | 5/1991 |
| FR | 2 749 754 A1 | 12/1997 |

* cited by examiner

*Primary Examiner*—Danny Worrell
(74) *Attorney, Agent, or Firm*—Jacobson Holman, PLLC

(57) ABSTRACT

The compressive orthosis comprises a leg portion (16) in a compressive knit suitable for delivering degressive therapeutic retention. The compressive knit comprises a net type knit knitted with a weft thread (22) of elastic material, advantageously in combination with at least one background thread (24, 26, 28), likewise in elastic material, and of smaller weight than the weft thread. The assembly forms a deformable array of substantially hexagonal cells (30) which, on being deformed, present greater elastic return force in the horizontal direction (H) than in the vertical direction (V).

9 Claims, 3 Drawing Sheets

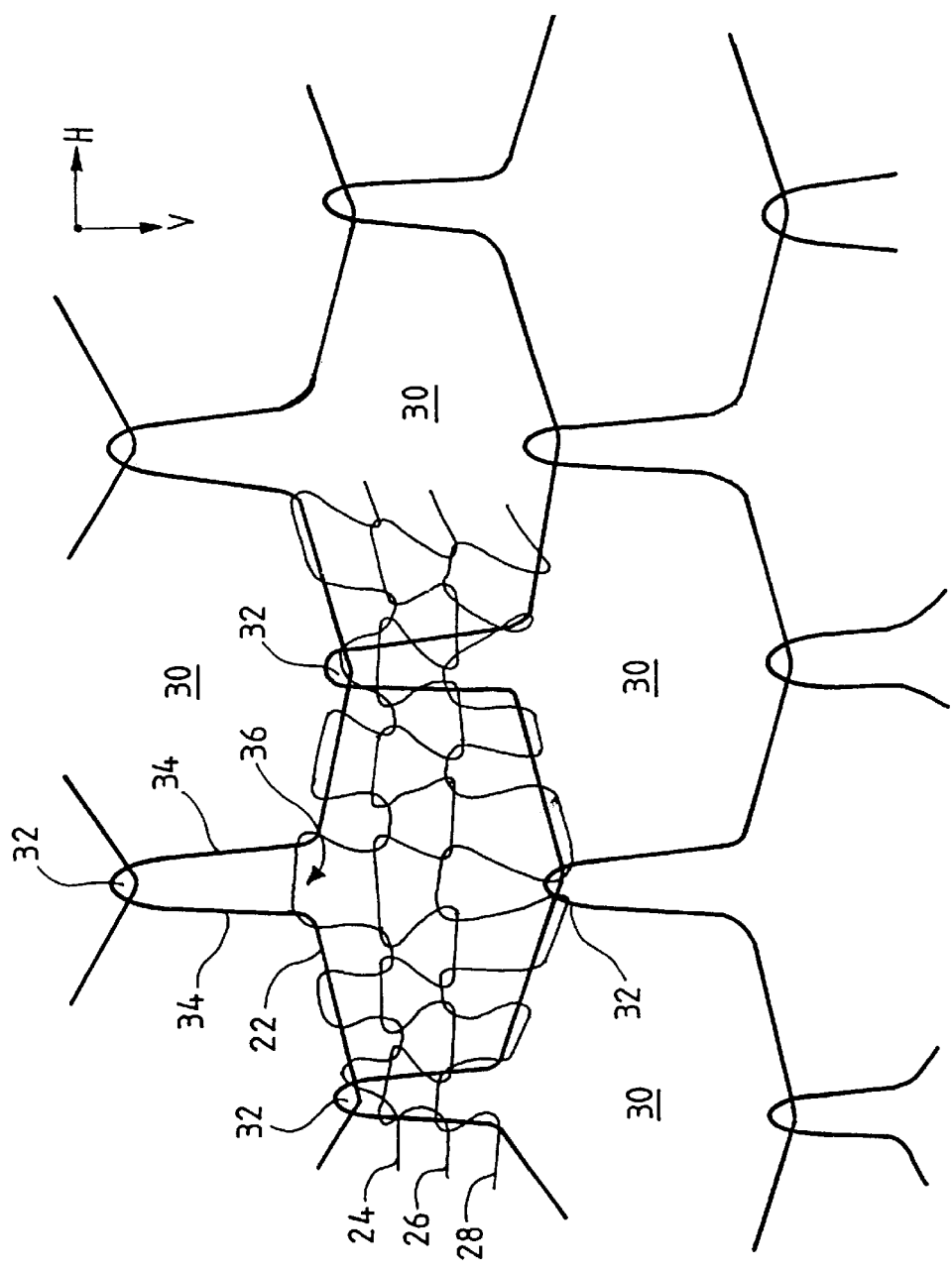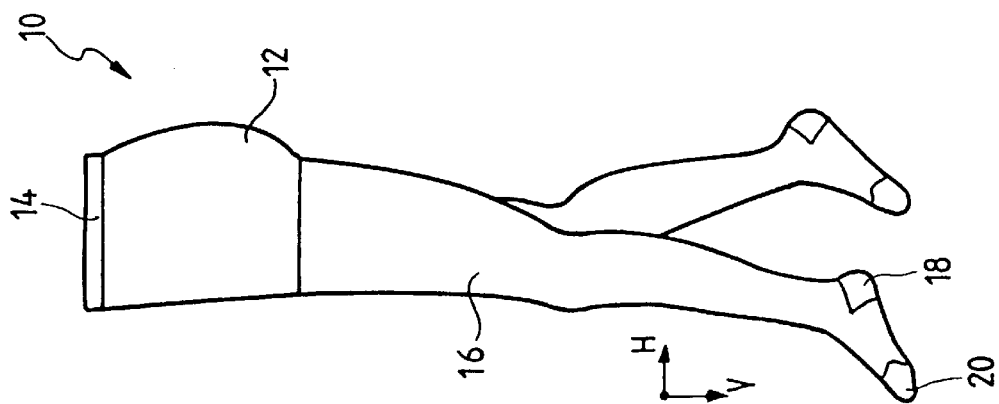

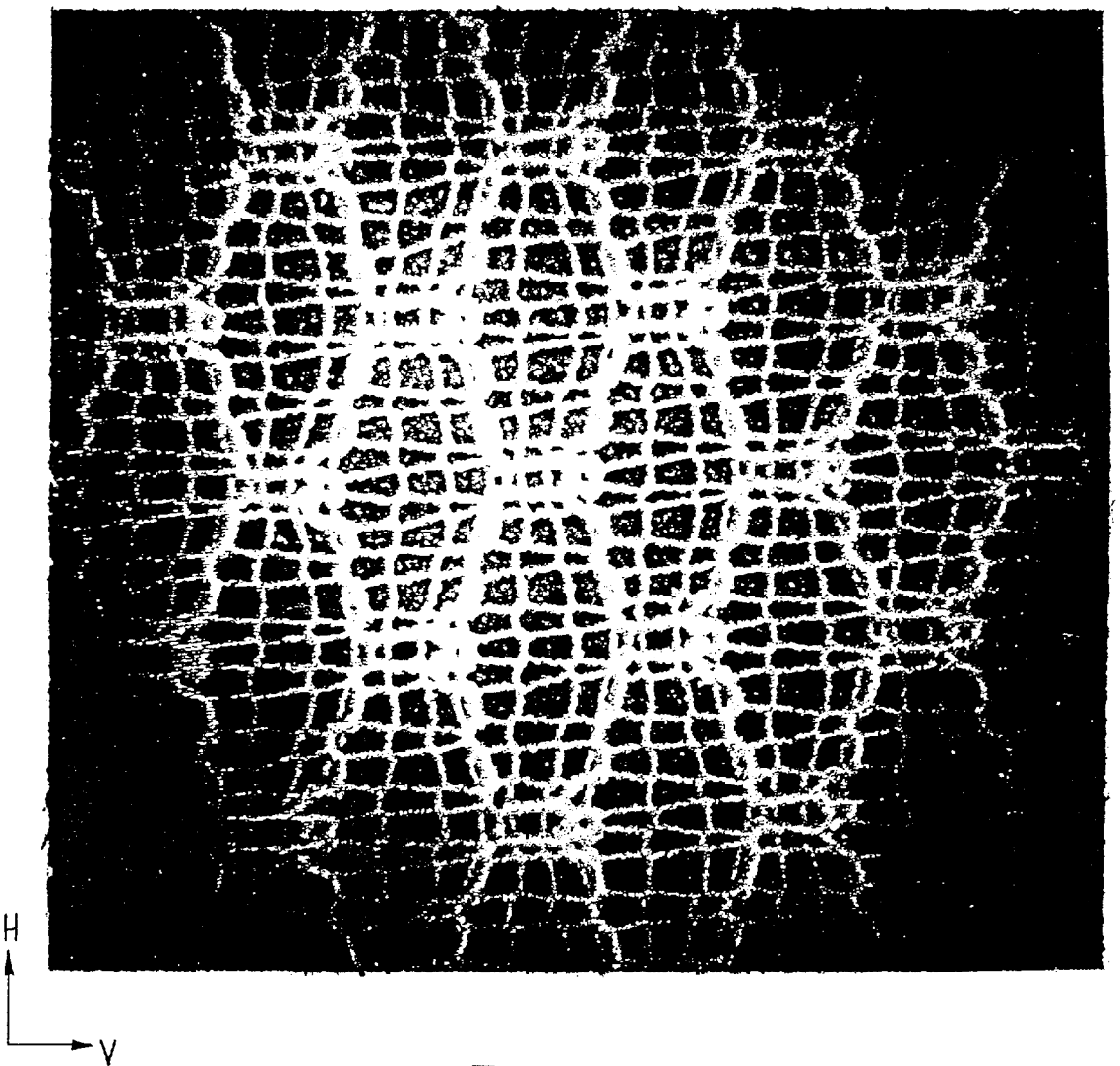
FIG_3

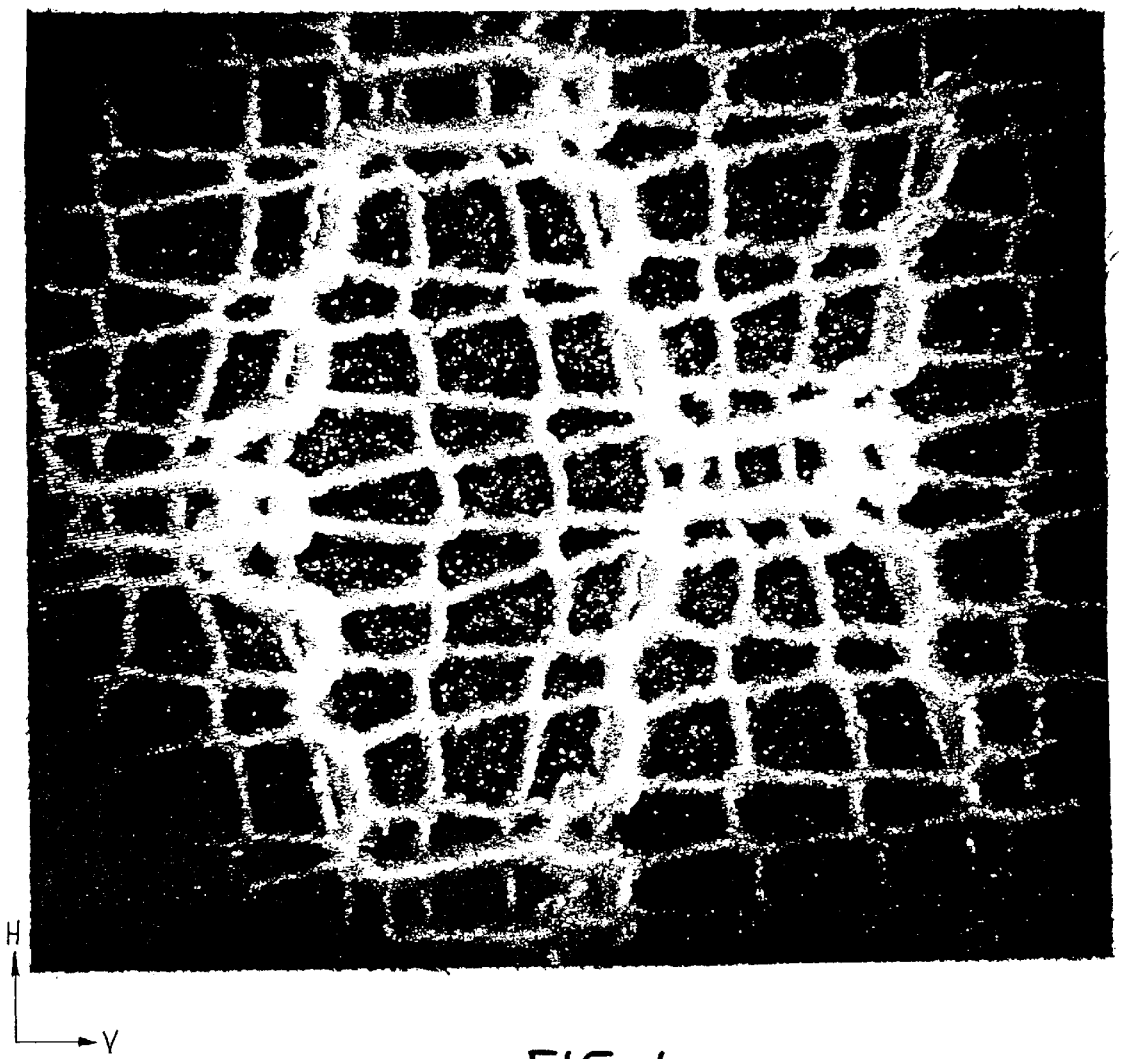
FIG_4

COMPRESSIVE ORTHOSIS SUCH AS RETENTION STOCKING OR TIGHTS

The invention relates to the field of compressive orthoses for one or both lower limbs, generally known as "elastic stockings" or "elastic tights".

Although the terms "stockings" and "tights" are used below, the invention is not limited to a particular article, but applies equally well to any compressive orthosis, whether in the form of tights (a single piece covering both lower limbs and the abdomen up to the waist), mono-tights (tights covering a single leg for applying remedial retention to a single lower limb), stockings (covering the thigh and the calf), or socks (covering the calves only).

To enable a high degree of compression to be applied to the lower limb(s), such articles are made of an elastic material, typically a knit having a very fine texture.

One of the drawbacks of a very fine texture is that it is relatively uncomfortable to wear, particularly when ambient temperature is high, typically in summer. Because of that discomfort, giving rise to sweating and irritation, patients tend to abandon such orthoses under these circumstances or at any rate to wear them less, even though continuous remedial retention, even on a reduced scale, is desirable, therapeutically speaking.

An object of the invention is to remedy that difficulty by proposing a novel type of compressive orthosis which, while providing the entire desired therapeutic effect (retention/compression to a therapeutic extent, and thus decreasing from the ankle), also provide the sensation of stockings that are cooler, better aired, thereby greatly improving the comfort of the patient, and consequently leading to treatment being complied with.

The compressive orthosis of the invention which is of the elastic stocking or tights type comprises a leg portion in a compressive knit suitable for delivering degressive therapeutic retention, and is characterized in that said compressive knit comprises a net type knit knitted with a weft thread of elastic material.

Most advantageously, the net type knit is combined with at least one background thread of elastic material and of lighter weight than the weft thread.

According to various preferred characteristics:

the knit comprises at least two background threads for each weft thread, and preferably three background threads for each weft thread, the background thread(s) being knitted together with the weft thread in such a manner as to form an array of cells that are substantially hexagonal, in particular an array which, on being deformed, presents a stronger resilient return force in the horizontal direction than in the vertical direction; and the ratio of the weight of the background thread to the weight of the weft thread is at least 1:3, and preferably about 1:4; with the weight of the weft thread being preferably about 130 dtex and that of the background thread about 33 dtex.

There follows a description of an embodiment of the invention given with reference to the accompanying drawings.

BRIEF DESCRIPTION OF THE DRAWINGS

FIG. 1 is a general view showing the various portions of elastic tights.

FIG. 2 is a detail view of the knit in accordance with the teaching of the invention.

FIG. 3 is a macrophotograph showing the texture of the stocking of the invention.

FIG. 4 is a magnification of the view of FIG. 3;

In FIG. 1, reference 10 is a general reference for elastic tights comprising, in conventional manner, a panty portion 12 with a waistband 14, and a leg portion 16 that is reinforced at 18 and 20 at the heel and the toes.

The panties 12 with the waistband 14, and also the reinforcement at the heels 18 and at the toes 20 are knitted in conventional manner, e.g. using a micromesh or a jersey knit, and are not described in detail below.

The leg portion 16 is designed to provide remedial or therapeutic retention, typically in class I or II (classes defined by French standards) with pressure at the ankle of about 10 millimeters of mercury (mmHg) to 15 mmHg (13.3 hPa to 20.0 hPa) in class I and 15 mmHg to 20 mmHg (20.0 hPa to 26.6 hPa) in class II. In addition, this pressure diminishes from the ankle to the thigh, with the pressure at the top of the leg being 50% smaller than the pressure at the ankle; the idea is to obtain a pressure gradient that tapers off regularly from the ankle to the thigh so as to facilitate venous return.

The leg portion 16 has a special knit making it possible to provide simultaneously both the above-defined desired medical retention and wearing qualities that are cooler and better aired than with the knits used for conventional elastic stockings or tights.

In a manner characteristic of the invention, this leg portion is made by knitting in a net pattern, e.g. by mesh filling and progressive double length knitting.

The knit makes use essentially of two types of thread, shown in greater detail in FIG. 2 and visible in the macrophotographs of FIGS. 3 and 4, namely:

a weft thread 22, e.g. an elastane thread weighing 130 dtex, which is double-covered with 28 dtex polyamide having 28 flat filaments; and one or more background threads 24, 26, and 28, typically elastane threads with 8 dtex double-coverings having 5 flat filaments and weighing 33 dtex (a weight which is typical for a conventional, non-therapeutic stocking).

The materials selected above (polyamide covered elastane with a composition 31% elastane+69% polyamide) is not limiting, and other compositions or proportions that can be used, e.g. elastane covered in cotton and polyamide, or indeed a mixture of elastane and elasto-diene (rubber latex).

For the background threads, or for the weft threads, or indeed for covering the background or the weft threads, it is also possible to use temperature regulating fibers such as Meryl® from Nylstar (hollow polyamide thread) or Tactel® from du Pont de Nemours (profile polyamide thread), or indeed a fiber containing "freshening" microcapsules that change phase.

The knit of the invention can be knitted on a programmable knitting machine having a 4 inch (10 cm) cylinder with 328 needles, with one row in four being constituted by the 130 dtex weft thread and the other three rows in four by the 33 dtex background threads.

Knitting is performed in such a manner as to cause the weft thread to make an array of substantially hexagonal cells 30. Successive rows of weft thread are interconnected at 32 (by knotting that is not visible in FIG. 2 in order to clarify the figure, but that is visible in the photographs of FIGS. 3 and 4). The two thread portions 34 extending on either side of such knotting 32 are held together at 36 by one of the background threads 34 so as to form one of the sides of the hexagon by moving the two portions 34 towards each other.

The knotting 32 makes it possible in particular to obtain sufficient retention, with the extensible nature of the knit being the result essentially of the elasticity of the weft thread more than the particular kind of knit.

The background threads 24, 26, 28 form a mesh that fills each of the cells 30 so as to build up a fine array giving texture to the stocking but without preventing elastic deformation thereof obtaining the desired retention.

In the figures, the directions V and H respectively indicate the vertical and horizontal orientations relative to a leg when the patient is standing. Thus, the weft threads 22 and the background threads 24, 26, and 28 all extend in the horizontal direction H (the direction of the weft thread), since it is elastic deformation in this direction that provides the desired retention.

The size of the cells 30 is selected as a function of the degree of retention that is desired, with a larger mesh size providing less retention for a given selection of threads than a smaller mesh size.

In a variant, in order to obtain higher retention pressure, it is possible for one of the background threads 24, 26, and/or 28 to be constituted by a non-elastic thread constituting a brake thread.

The desired therapeutic effect (effective pressure and pressure tapering from the ankle) is fully conserved, so the therapeutic indications for elastic stockings or tights of the invention are identical to those for conventional stockings or tights, typically in classes I or II.

What is claimed is:

1. A compressive orthosis of the elastic stocking or tight type having, a leg portion (16) in a compressive knit suitable for delivering degressive therapeutic retention, the orthosis being characterized in that said compressive knit comprises a net type knit knitted from successive rows of weft thread (22) of elastic material, said rows being interconnected by knotting (32) so as to make an array of cells (3), and from a mesh of background threads (24, 26, 28) knitted so as to fill said cells.

2. The compressive orthosis of claim 1, in which then the type knit is combined with at least one background thread (24, 26 28) of elastic material, and of smaller weight than the weft thread.

3. The compressive orthosis of claim 2, in which the knit comprises at least two background threads for each weft thread.

4. The compressive orthosis of claim 3, in which the knit comprises three background threads (24, 26 28) for each weft thread (22).

5. The compressive orthosis of claim 3, in which the background threads are knitted with the weft thread in such a manner as to co-operate therewith to form a deformable array of substantially hexagonal cells (30).

6. The compressive orthosis of claim 5, in which the deformable array, on being deformed, presents a greater resilient return force in a horizontal direction (H) than in a vertical direction (V).

7. The compressive orthosis of claim 2, in which the weight ratio of the background thread to the weft thread is at least 1:3.

8. The compressive orthosis of claim 7, wherein the weight ration is about 1:4.

9. The compressive orthosis claim 7, in which the weight of the weft thread is about 130 dtex and the weight of the background thread is about 33 dtex.

* * * * *